US012747268B2

(12) United States Patent
Kim et al.

(10) Patent No.: US 12,747,268 B2
(45) Date of Patent: *Sep. 29, 2026

(54) HIGH-POTENCY SARS CORONAVIRUS 2 ANTIGEN AND VACCINE COMPOSITION COMPRISING SAME

(71) Applicant: KOREA RESEARCH INSTITUTE OF CHEMICAL TECHNOLOGY, Daejeon (KR)

(72) Inventors: Seong Jun Kim, Daejeon (KR); Chonsaeng Kim, Daejeon (KR); Kyun Do Kim, Daejeon (KR); Dae Gyun Ahn, Daejeon (KR); Young Chan Kwon, Daejeon (KR); Keunbon Ku, Daejeon (KR); Hae Soo Kim, Daejeon (KR); Hye Jin Shin, Daejeon (KR); Gun Young Yoon, Daejeon (KR); In Su Hwang, Daejeon (KR); Gi Uk Jeong, Daejeon (KR); Sun Hee Lee, Daejeon (KR); Mi Hwa Kim, Daejeon (KR); Su Min Lee, Daejeon (KR); Bum Tae Kim, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 876 days.

This patent is subject to a terminal disclaimer.

(21) Appl. No.: 17/998,729

(22) PCT Filed: May 13, 2021

(86) PCT No.: PCT/KR2021/005984

§ 371 (c)(1),
(2) Date: Nov. 14, 2022

(87) PCT Pub. No.: WO2021/230668

PCT Pub. Date: Nov. 18, 2021

(65) Prior Publication Data

US 2023/0220012 A1 Jul. 13, 2023

(30) Foreign Application Priority Data

May 14, 2020 (KR) ........................ 10-2020-0057768

(51) Int. Cl.
*C07K 14/005* (2006.01)
*A61K 39/215* (2006.01)
*A61P 31/14* (2006.01)

(52) U.S. Cl.
CPC .......... *C07K 14/005* (2013.01); *A61K 39/215* (2013.01); *A61P 31/14* (2018.01); *C07K 2319/03* (2013.01); *C12N 2770/20022* (2013.01); *C12N 2770/20034* (2013.01)

(58) Field of Classification Search
CPC .............. C07K 14/005; C07K 2319/03; C07K 14/705; C07K 2319/10; C07K 2319/40; A61K 39/215; A61K 2039/575; A61K 39/12; A61P 31/14; C12N 2770/20022; C12N 2770/20034; C12N 15/62
See application file for complete search history.

(56) References Cited

U.S. PATENT DOCUMENTS

| | | | | |
|---|---|---|---|---|
| 8,673,313 | B2 | 3/2014 | Madrazo et al. | |
| 2015/0218569 | A1* | 8/2015 | Numata | C07K 7/06 435/468 |
| 2021/0322541 | A1* | 10/2021 | Akahata | A61K 39/12 |
| 2022/0306718 | A1* | 9/2022 | Kim | C07K 19/00 |
| 2023/0149535 | A1* | 5/2023 | Kulp | A61P 37/04 424/221.1 |

FOREIGN PATENT DOCUMENTS

| | | | |
|---|---|---|---|
| CN | 107841507 | A | 3/2018 |
| KR | 1020170128516 | A | 11/2017 |
| WO | 2010129033 | A2 | 11/2010 |

OTHER PUBLICATIONS

Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*
Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*
Sela-Culang I, Kunik V, Ofran Y. The structural basis of antibody-antigen recognition. Front Immunol. Oct. 8, 2013;4:302. (Year: 2013).*

(Continued)

*Primary Examiner* — Rachel B Gill
(74) *Attorney, Agent, or Firm* — Vorys, Sater, Seymour and Pease LLP; Mih Suhn Koh

(57) ABSTRACT

Provided are a recombinant antigen comprising a cell membrane permeation domain comprising a polypeptide of any one of SEQ ID NOs: 1 to 22 derived from human LRRC24 and a SARS-CoV-2 antigen or a fragment thereof, a vaccine composition comprising the recombinant antigen, a gene construct comprising a polynucleotide encoding the recombinant antigen, a recombinant vector comprising the gene construct, a method for producing the SARS-CoV-2 recombinant antigen, and a kit for preventing or treating SARS-CoV-2 infection comprising the vaccine composition and users' instruction thereof, wherein the antigen exhibited higher immunogenicity against SARS-CoV-2 the neutralizing antibody was better formed in actual animal experiments, excellent protective immunity was induced, and toxicity did not appear in the toxicity test.

10 Claims, 6 Drawing Sheets

Specification includes a Sequence Listing.

(56) References Cited

OTHER PUBLICATIONS

Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714. (Year : 2015).*

Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*

Jahirul Islam M, Nawal Islam N, Siddik Alom M, Kabir M, Halim MA. A review on structural, non-structural, and accessory proteins of SARS-CoV-2: Highlighting drug target sites. Immunobiology. Jan. 2023;228(1):152302. Epub Nov. 15, 2022. (Year: 2022).*

Qiao R, Li J, Gong J, Shao Y, Yu J, Chen Y, Lu Y, Yang L, Lin L, Hu Z, Wang P, Zhao X, Zhang W. Evolving SARS-CoV-2 Vaccines: From Current Solutions to Broad-Spectrum Protection. Vaccines (Basel). Jun. 12, 2025;13(6):635. (Year: 2025) .*

Wrapp D, Wang N, Corbett KS, Goldsmith JA, Hsieh CL, Abiona O, Graham BS, McLellan JS. Cryo-EM structure of the 2019-nCoV spike in the prefusion conformation. Science. Mar. 13, 2020;367(6483):1260-1263. Epub Feb. 19, 2020. (Year: 2020).*

Jiang, Antibodies induced by receptor-binding domain in spike protein of SARS-CoV do not cross-neutralize the novel human coronavirus hCoV-EMC, Letters to the Editor: Journal of Infection, 2013, vol. 67, No. 4, pp. 348-350.

Li et al., Structure of SARS Coronavirus Spike Receptor-Binding Domain Complexed with Receptor, Science, vol. 309, No. 5742, pp. 1864-1868.

Lu et al., Genomic characterisation and epidemiology of 2019 novel coronavirus: implications for virus origins and receptor binding, Lancet, 2020, vol. 395, No. 10224, pp. 565-574.

Ou et al., Crystal structure of the receptor binding domain of the spike glycoprotein of human betacoronavirus HKU1, Nature Communications, 2017, vol. 8, No. 15216, 10 pages.

Yang et al., Cell-Penetrating Peptides: Efficient Vectors for Vaccine Delivery, Current Drug Delivery, 2019, vol. 16, pp. 430-443.

* cited by examiner

[Fig. 1a]

Consensus
1. 2019 nCoV RBD
2. SARS RBD

```
                  10        20        30        40        50        60        70        80
1    1   RVQPTESIVRFPNITNLCPFGEVFNATRFASVYAWNRKRISNCVADYSVLYNSASFSTFKCYGVSPTKLNDLCFTNVYAD  80
         RV P+  +VRFPNITNLCPFGEVFNAT+F SVYAW RK+ISNCVADYSVLYNS  FSTFKCYGVS TKLNDLCF+NVYAD
2    1   RVVPSGDVVRFPNITNLCPFGEVFNATKFPSVYAWERKKISNCVADYSVLYNSTFFSTFKCYGVSATKLNDLCFSNVYAD  80
                  10        20        30        40        50        60        70        80

                  90       100       110       120       130       140       150       160
1   81   SFVIRGDEVRQIAPGQTGKIADYNYKLPDDFTGCVIAWNSNNLDSKVGGNYNYLYRLFRKSNLKPFERDISTEIYQAGST  160
         SFV++GD+VRQIAPGQTG IADYNYKLPDDF GCV+AWN+ N+D+   GNYNY YR  R   L+PFERDIS   +
2   81   SFVVKGDDVRQIAPGQTGVIADYNYKLPDDFMGCVLAWNTRNIDATSTGNYNYKYRYLRHGKLRPFERDISNVPFSPDGK  160
                  90       100       110       120       130       140       150       160

                 170       180       190       200       210       220
1  161   PCNGVEGFNCYFPLQSYGFQPTNGVGYQPYRVVVLSFELLHAPATVCGPKKSTNLVKNKCVNF  223
         PC      NCY+PL  YGF  T G+GYQPYRVVVLSFELL+APATVCGPK ST+L+KN+CVNF
2  161   PCT-PPALNCYWPLNDYGFYTTTGIGYQPYRVVVLSFELLNAPATVCGPKLSTDLIKNQCVNF  222
                  170       180       190       200       210       220
```

[Fig. 1b]
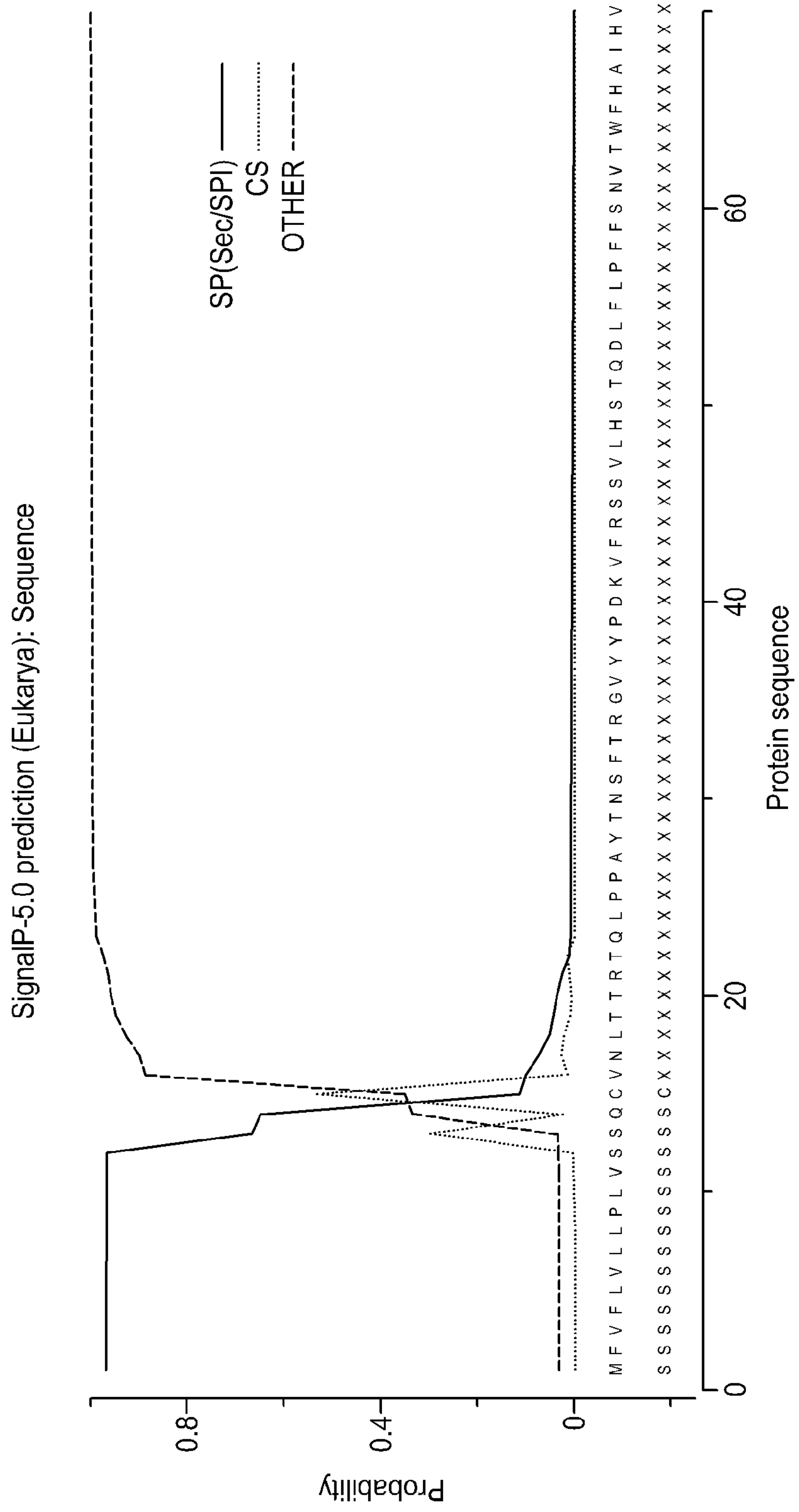

[Fig. 1c]
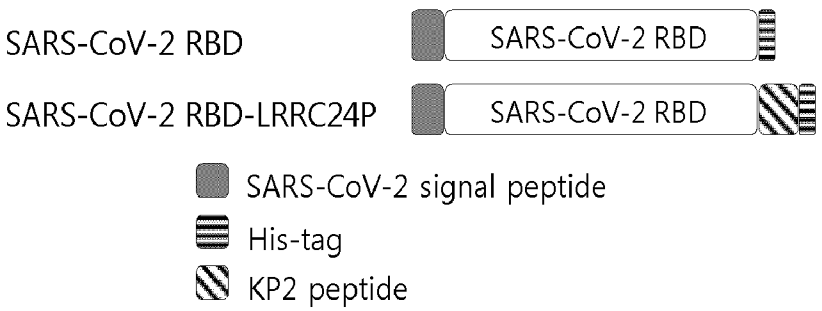

[Fig. 2]
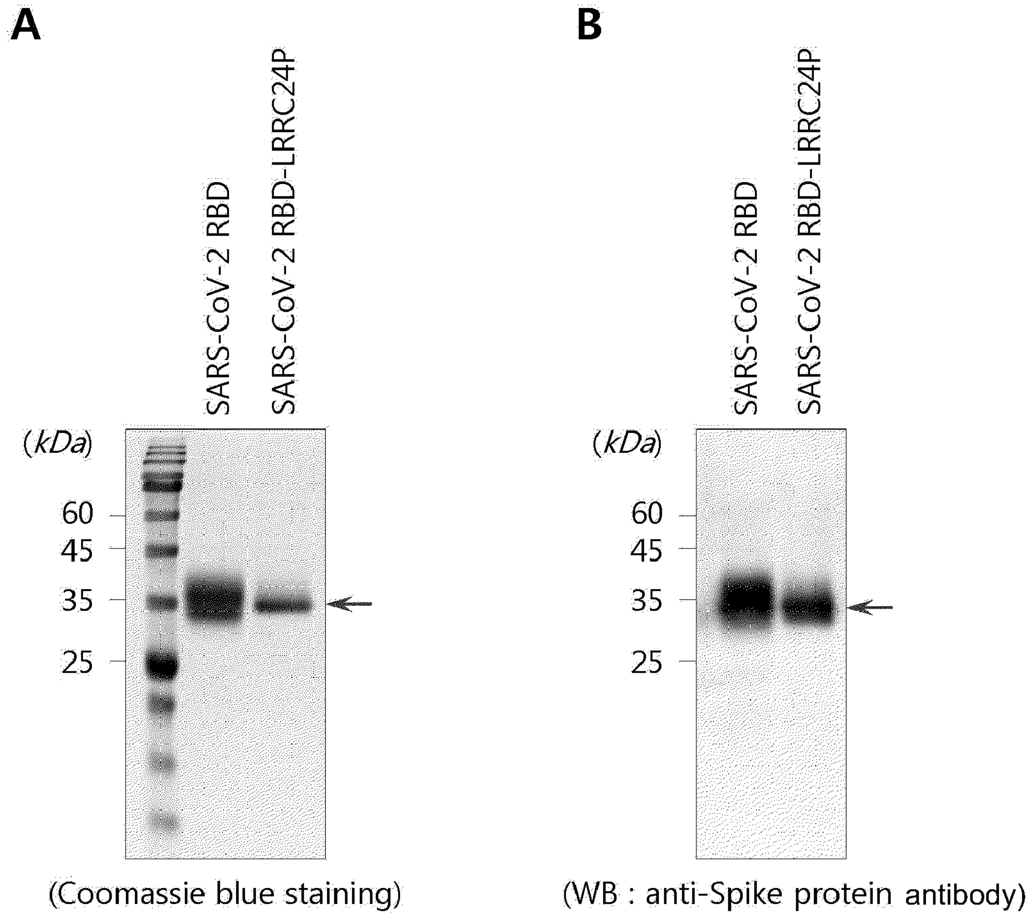

[Fig. 3]
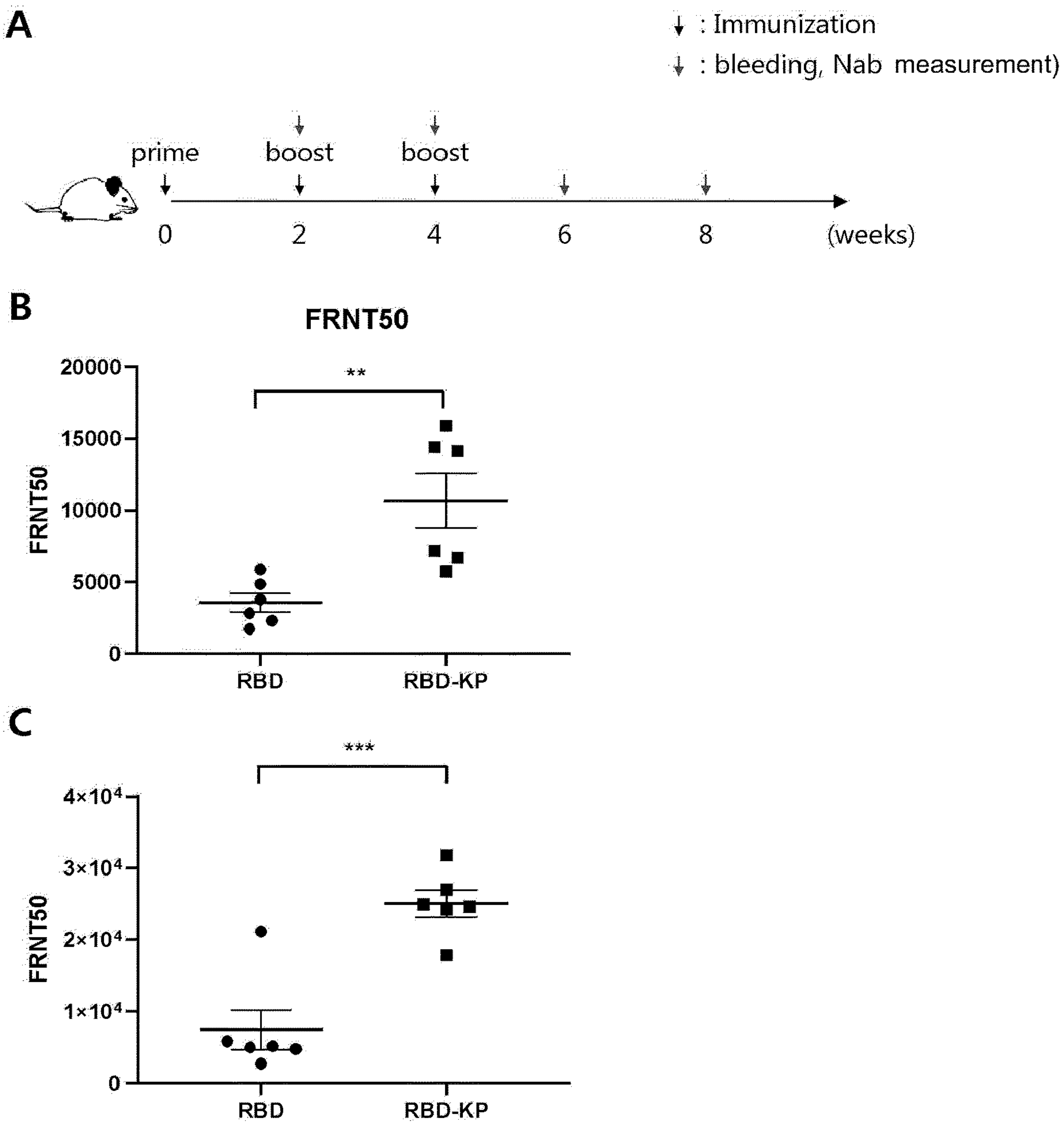

[Fig. 4]
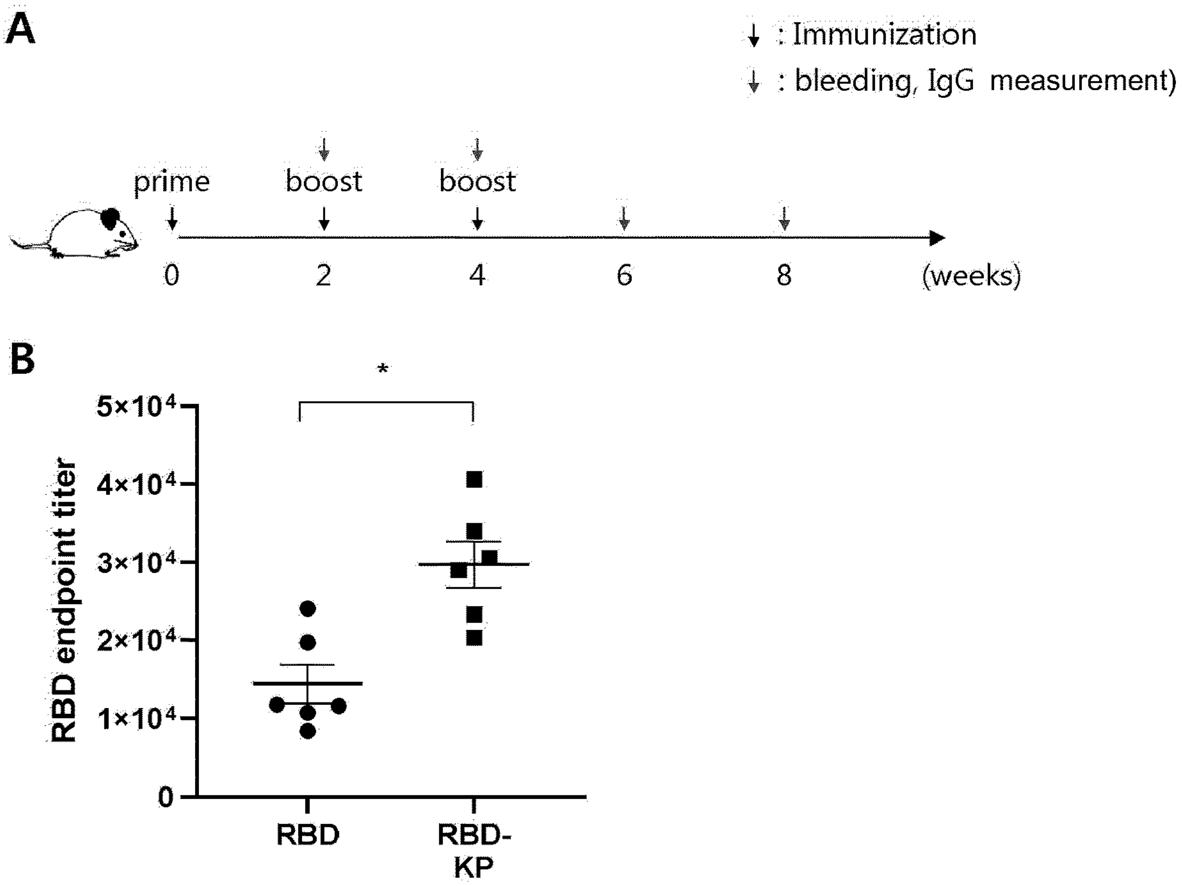

```
                     SEQUENCE LISTING


<160> NUMBER OF SEQ ID NOS: 50

<210> SEQ ID NO 1
<211> LENGTH: 10
<212> TYPE: PRT
<213> ORGANISM: Artificial Sequence
<220> FEATURE:
<223> OTHER INFORMATION: LRRC24P

<400> SEQUENCE: 1

Arg Arg Arg Arg Arg Arg Lys Lys Ala Arg
1               5                   10


<210> SEQ ID NO 2
<211> LENGTH: 10
<212> TYPE: PRT
<213> ORGANISM: Artificial Sequence
<220> FEATURE:
<223> OTHER INFORMATION: LRRC24P-M1

<400> SEQUENCE: 2

Arg Arg Arg Arg Arg Arg Lys Lys Ser Arg
1               5                   10


<210> SEQ ID NO 3
<211> LENGTH: 10
<212> TYPE: PRT
<213> ORGANISM: Artificial Sequence
<220> FEATURE:
<223> OTHER INFORMATION: LRRC24P-M2

<400> SEQUENCE: 3

Arg Arg Arg Arg Arg Arg Lys Lys Val Arg
1               5                   10


<210> SEQ ID NO 4
<211> LENGTH: 10
<212> TYPE: PRT
<213> ORGANISM: Artificial Sequence
<220> FEATURE:
<223> OTHER INFORMATION: LRRC24P-M3

<400> SEQUENCE: 4

Arg Arg Arg Arg Arg Arg Lys Lys Tyr Arg
1               5                   10


<210> SEQ ID NO 5
<211> LENGTH: 10
<212> TYPE: PRT
<213> ORGANISM: Artificial Sequence
<220> FEATURE:
<223> OTHER INFORMATION: LRRC24P-M4

<400> SEQUENCE: 5

Arg Arg Arg Arg Arg Arg Lys Lys Glu Arg
1               5                   10
```

<210> SEQ ID NO 6
<211> LENGTH: 10
<212> TYPE: PRT
<213> ORGANISM: Artificial Sequence
<220> FEATURE:
<223> OTHER INFORMATION: LRRC24P-M5

<400> SEQUENCE: 6

Arg Arg Arg Arg Arg Arg Lys Lys Gln Arg
1 5 10

<210> SEQ ID NO 7
<211> LENGTH: 10
<212> TYPE: PRT
<213> ORGANISM: Artificial Sequence
<220> FEATURE:
<223> OTHER INFORMATION: LRRC24P-M6

<400> SEQUENCE: 7

Arg Arg Arg Arg Arg Arg Lys Lys Arg Arg
1 5 10

<210> SEQ ID NO 8
<211> LENGTH: 10
<212> TYPE: PRT
<213> ORGANISM: Artificial Sequence
<220> FEATURE:
<223> OTHER INFORMATION: LRRC24P-MN

<400> SEQUENCE: 8

Arg Arg Arg Arg Arg Arg Lys Lys Asn Arg
1 5 10

<210> SEQ ID NO 9
<211> LENGTH: 10
<212> TYPE: PRT
<213> ORGANISM: Artificial Sequence
<220> FEATURE:
<223> OTHER INFORMATION: LRRC24P-MD

<400> SEQUENCE: 9

Arg Arg Arg Arg Arg Arg Lys Lys Asp Arg
1 5 10

<210> SEQ ID NO 10
<211> LENGTH: 10
<212> TYPE: PRT
<213> ORGANISM: Artificial Sequence
<220> FEATURE:
<223> OTHER INFORMATION: LRRC24P-MC

<400> SEQUENCE: 10

Arg Arg Arg Arg Arg Arg Lys Lys Cys Arg
1 5 10

<210> SEQ ID NO 11
<211> LENGTH: 10
<212> TYPE: PRT
<213> ORGANISM: Artificial Sequence
<220> FEATURE:
<223> OTHER INFORMATION: LRRC24P-MG

<400> SEQUENCE: 11

Arg Arg Arg Arg Arg Arg Lys Lys Gly Arg
1 5 10

```
<210> SEQ ID NO 12
<211> LENGTH: 10
<212> TYPE: PRT
<213> ORGANISM: Artificial Sequence
<220> FEATURE:
<223> OTHER INFORMATION: LRRC24P-MH

<400> SEQUENCE: 12

Arg Arg Arg Arg Arg Arg Lys Lys His Arg
1               5                   10


<210> SEQ ID NO 13
<211> LENGTH: 10
<212> TYPE: PRT
<213> ORGANISM: Artificial Sequence
<220> FEATURE:
<223> OTHER INFORMATION: LRRC24P-MI

<400> SEQUENCE: 13

Arg Arg Arg Arg Arg Arg Lys Lys Ile Arg
1               5                   10


<210> SEQ ID NO 14
<211> LENGTH: 10
<212> TYPE: PRT
<213> ORGANISM: Artificial Sequence
<220> FEATURE:
<223> OTHER INFORMATION: LRRC24P-ML

<400> SEQUENCE: 14

Arg Arg Arg Arg Arg Arg Lys Lys Leu Arg
1               5                   10


<210> SEQ ID NO 15
<211> LENGTH: 10
<212> TYPE: PRT
<213> ORGANISM: Artificial Sequence
<220> FEATURE:
<223> OTHER INFORMATION: LRRC24P-MK

<400> SEQUENCE: 15

Arg Arg Arg Arg Arg Arg Lys Lys Lys Arg
1               5                   10


<210> SEQ ID NO 16
<211> LENGTH: 10
<212> TYPE: PRT
<213> ORGANISM: Artificial Sequence
<220> FEATURE:
<223> OTHER INFORMATION: LRRC24P-MM

<400> SEQUENCE: 16

Arg Arg Arg Arg Arg Arg Lys Lys Met Arg
1               5                   10


<210> SEQ ID NO 17
<211> LENGTH: 10
<212> TYPE: PRT
<213> ORGANISM: Artificial Sequence
<220> FEATURE:
<223> OTHER INFORMATION: LRRC24P-MF

<400> SEQUENCE: 17

Arg Arg Arg Arg Arg Arg Lys Lys Phe Arg
1               5                   10
```

<210> SEQ ID NO 18
<211> LENGTH: 10
<212> TYPE: PRT
<213> ORGANISM: Artificial Sequence
<220> FEATURE:
<223> OTHER INFORMATION: LRRC24P-MP

<400> SEQUENCE: 18

Arg Arg Arg Arg Arg Arg Lys Lys Pro Arg
1 5 10

<210> SEQ ID NO 19
<211> LENGTH: 10
<212> TYPE: PRT
<213> ORGANISM: Artificial Sequence
<220> FEATURE:
<223> OTHER INFORMATION: LRRC24P-MT

<400> SEQUENCE: 19

Arg Arg Arg Arg Arg Arg Lys Lys Thr Arg
1 5 10

<210> SEQ ID NO 20
<211> LENGTH: 10
<212> TYPE: PRT
<213> ORGANISM: Artificial Sequence
<220> FEATURE:
<223> OTHER INFORMATION: LRRC24P-MW

<400> SEQUENCE: 20

Arg Arg Arg Arg Arg Arg Lys Lys Trp Arg
1 5 10

<210> SEQ ID NO 21
<211> LENGTH: 9
<212> TYPE: PRT
<213> ORGANISM: Artificial Sequence
<220> FEATURE:
<223> OTHER INFORMATION: LRRC24P-M7

<400> SEQUENCE: 21

Arg Arg Arg Arg Arg Lys Lys Ala Arg
1 5

<210> SEQ ID NO 22
<211> LENGTH: 9
<212> TYPE: PRT
<213> ORGANISM: Artificial Sequence
<220> FEATURE:
<223> OTHER INFORMATION: LRRC24P-M8

<400> SEQUENCE: 22

Arg Arg Arg Arg Arg Arg Lys Lys Ala
1 5

<210> SEQ ID NO 23
<211> LENGTH: 741
<212> TYPE: DNA
<213> ORGANISM: Artificial Sequence
<220> FEATURE:
<223> OTHER INFORMATION: SARS-CoV-2 RBD nucleotide

<400> SEQUENCE: 23
atgtttgtct tcctcgttct gctcccactt gtaagctctc aatgcgtccg ggtacaaccc 60
acagaatcaa ttgtcagatt tcccaatatc actaacctgt gtccctttgg cgaagtgttt 120
aatgccaccc gctttgcatc cgtctatgcg tggaacagga aaaggatatc caactgtgtg 180

```
gcagactatt ccgtccttta caattcagct tcctttagta cttttaagtg ttacggggtt    240

tcaccaacaa aactgaacga tctctgtttc actaatgtat atgctgactc ttttgtcata    300

cgcggtgatg aggttaggca aatagcgccc ggccagacag gcaaaatagc ggattacaac    360

tataaacttc ctgatgactt cacgggatgc gttatagcat ggaacagtaa caacctcgat    420

tcaaaggttg gggaaacta caattacctc tatcgattgt tccgaaagag taacctcaag    480

ccctttgagc gcgacatctc aacggagata tatcaagctg gatctacgcc ctgcaatggg    540

gtagaggggt ttaattgtta cttcccactg caaagttatg gctttcagcc aacgaacggc    600

gttgggtatc aaccatatcg ggtggtagtg ctttcattcg aactgcttca tgcacccgca    660

acggtctgcg gtccgaaaaa gagcactaac ctggtcaaga ataaatgcgt taatttcact    720

agtcatcacc atcaccatca c                                              741
```

<210> SEQ ID NO 24
<211> LENGTH: 247
<212> TYPE: PRT
<213> ORGANISM: Artificial Sequence
<220> FEATURE:
<223> OTHER INFORMATION: SARS-CoV-2 RBD amino acid

<400> SEQUENCE: 24

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser His His His His His His
                245
```

<210> SEQ ID NO 25
<211> LENGTH: 771
<212> TYPE: DNA
<213> ORGANISM: Artificial Sequence
<220> FEATURE:
<223> OTHER INFORMATION: SARS-CoV-2 RBD-LRRC24P nucleotides

<400> SEQUENCE: 25

```
atgtttgtct tcctcgttct gctcccactt gtaagctctc aatgcgtccg ggtacaaccc      60

acagaatcaa ttgtcagatt tcccaatatc actaacctgt gtccctttgg cgaagtgttt     120

aatgccaccc gctttgcatc cgtctatgcg tggaacagga aaaggatatc caactgtgtg     180

gcagactatt ccgtccttta caattcagct tcctttagta cttttaagtg ttacggggtt     240

tcaccaacaa aactgaacga tctctgtttc actaatgtat atgctgactc ttttgtcata     300

cgcggtgatg aggttaggca aatagcgccc ggccagacag gcaaaatagc ggattacaac     360

tataaacttc ctgatgactt cacgggatgc gttatagcat ggaacagtaa caacctcgat     420

tcaaaggttg gggaaacta caattacctc tatcgattgt tccgaaagag taacctcaag     480

ccctttgagc gcgacatctc aacggagata tatcaagctg gatctacgcc ctgcaatggg     540

gtagaggggt ttaattgtta cttcccactg caaagttatg gctttcagcc aacgaacggc     600

gttgggtatc aaccatatcg ggtggtagtg ctttcattcg aactgcttca tgcacccgca     660

acggtctgcg gtccgaaaaa gagcactaac ctggtcaaga ataaatgcgt taatttcact     720

agtcgaagaa gacgaaggag aaagaaagct aggcatcacc atcaccatca c              771
```

<210> SEQ ID NO 26
<211> LENGTH: 257
<212> TYPE: PRT
<213> ORGANISM: Artificial Sequence
<220> FEATURE:
<223> OTHER INFORMATION: SARS-CoV-2 RBD-LRRC24P amino acid

<400> SEQUENCE: 26

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175
```

-continued

```
Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Ala Arg His His His His His
                245                 250                 255

His


<210> SEQ ID NO 27
<211> LENGTH: 257
<212> TYPE: PRT
<213> ORGANISM: Artificial Sequence
<220> FEATURE:
<223> OTHER INFORMATION: SARS-CoV-2 RBD-LRRC24P-M1

<400> SEQUENCE: 27

Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Ser Arg His His His His His
                245                 250                 255

His


<210> SEQ ID NO 28
```

<211> LENGTH: 257
<212> TYPE: PRT
<213> ORGANISM: Artificial Sequence
<220> FEATURE:
<223> OTHER INFORMATION: SARS-CoV-2 RBD-LRRC24P-M2

<400> SEQUENCE: 28

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Val Arg His His His His His
                245                 250                 255

His
```

<210> SEQ ID NO 29
<211> LENGTH: 257
<212> TYPE: PRT
<213> ORGANISM: Artificial Sequence
<220> FEATURE:
<223> OTHER INFORMATION: SARS-CoV-2 RBD-LRRC24P-M3

<400> SEQUENCE: 29

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60
```

```
Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Tyr Arg His His His His His
                245                 250                 255

His


<210> SEQ ID NO 30
<211> LENGTH: 257
<212> TYPE: PRT
<213> ORGANISM: Artificial Sequence
<220> FEATURE:
<223> OTHER INFORMATION: SARS-CoV-2 RBD-LRRC24P-M4

<400> SEQUENCE: 30

Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160
```

-continued

```
Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Glu Arg His His His His His
                245                 250                 255

His


<210> SEQ ID NO 31
<211> LENGTH: 257
<212> TYPE: PRT
<213> ORGANISM: Artificial Sequence
<220> FEATURE:
<223> OTHER INFORMATION: SARS-CoV-2 RBD-LRRC24P-M5

<400> SEQUENCE: 31

Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Gln Arg His His His His His
                245                 250                 255

His
```

<210> SEQ ID NO 32
<211> LENGTH: 257
<212> TYPE: PRT
<213> ORGANISM: Artificial Sequence
<220> FEATURE:
<223> OTHER INFORMATION: SARS-CoV-2 RBD-LRRC24P-M6

<400> SEQUENCE: 32

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Arg Arg His His His His His
                245                 250                 255

His
```

<210> SEQ ID NO 33
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MN

<400> SEQUENCE: 33

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45
```

```
Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Asn Arg His His His His His
                245                 250                 255

His


<210> SEQ ID NO 34
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MD

<400> SEQUENCE: 34

Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140
```

Gly Asn Tyr Asn Tyr Leu Tyr Arg Leu Phe Arg Lys Ser Asn Leu Lys
145 150 155 160

Pro Phe Glu Arg Asp Ile Ser Thr Glu Ile Tyr Gln Ala Gly Ser Thr
165 170 175

Pro Cys Asn Gly Val Glu Gly Phe Asn Cys Tyr Phe Pro Leu Gln Ser
180 185 190

Tyr Gly Phe Gln Pro Thr Asn Gly Val Gly Tyr Gln Pro Tyr Arg Val
195 200 205

Val Val Leu Ser Phe Glu Leu Leu His Ala Pro Ala Thr Val Cys Gly
210 215 220

Pro Lys Lys Ser Thr Asn Leu Val Lys Asn Lys Cys Val Asn Phe Thr
225 230 235 240

Ser Arg Arg Arg Arg Arg Arg Lys Lys Asp Arg His His His His His
245 250 255

His

<210> SEQ ID NO 35
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MC

<400> SEQUENCE: 35

Met Phe Val Phe Leu Val Leu Leu Pro Leu Val Ser Ser Gln Cys Val
1 5 10 15

Arg Val Gln Pro Thr Glu Ser Ile Val Arg Phe Pro Asn Ile Thr Asn
20 25 30

Leu Cys Pro Phe Gly Glu Val Phe Asn Ala Thr Arg Phe Ala Ser Val
35 40 45

Tyr Ala Trp Asn Arg Lys Arg Ile Ser Asn Cys Val Ala Asp Tyr Ser
50 55 60

Val Leu Tyr Asn Ser Ala Ser Phe Ser Thr Phe Lys Cys Tyr Gly Val
65 70 75 80

Ser Pro Thr Lys Leu Asn Asp Leu Cys Phe Thr Asn Val Tyr Ala Asp
85 90 95

Ser Phe Val Ile Arg Gly Asp Glu Val Arg Gln Ile Ala Pro Gly Gln
100 105 110

Thr Gly Lys Ile Ala Asp Tyr Asn Tyr Lys Leu Pro Asp Asp Phe Thr
115 120 125

Gly Cys Val Ile Ala Trp Asn Ser Asn Asn Leu Asp Ser Lys Val Gly
130 135 140

Gly Asn Tyr Asn Tyr Leu Tyr Arg Leu Phe Arg Lys Ser Asn Leu Lys
145 150 155 160

Pro Phe Glu Arg Asp Ile Ser Thr Glu Ile Tyr Gln Ala Gly Ser Thr
165 170 175

Pro Cys Asn Gly Val Glu Gly Phe Asn Cys Tyr Phe Pro Leu Gln Ser
180 185 190

Tyr Gly Phe Gln Pro Thr Asn Gly Val Gly Tyr Gln Pro Tyr Arg Val
195 200 205

Val Val Leu Ser Phe Glu Leu Leu His Ala Pro Ala Thr Val Cys Gly
210 215 220

Pro Lys Lys Ser Thr Asn Leu Val Lys Asn Lys Cys Val Asn Phe Thr
225 230 235 240

Ser Arg Arg Arg Arg Arg Arg Lys Lys Cys Arg His His His His His 245 250 255

His

<210> SEQ ID NO 36
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MG

<400> SEQUENCE: 36

Met Phe Val Phe Leu Val Leu Leu Pro Leu Val Ser Ser Gln Cys Val
1 5 10 15

Arg Val Gln Pro Thr Glu Ser Ile Val Arg Phe Pro Asn Ile Thr Asn
20 25 30

Leu Cys Pro Phe Gly Glu Val Phe Asn Ala Thr Arg Phe Ala Ser Val
35 40 45

Tyr Ala Trp Asn Arg Lys Arg Ile Ser Asn Cys Val Ala Asp Tyr Ser
50 55 60

Val Leu Tyr Asn Ser Ala Ser Phe Ser Thr Phe Lys Cys Tyr Gly Val
65 70 75 80

Ser Pro Thr Lys Leu Asn Asp Leu Cys Phe Thr Asn Val Tyr Ala Asp
85 90 95

Ser Phe Val Ile Arg Gly Asp Glu Val Arg Gln Ile Ala Pro Gly Gln
100 105 110

Thr Gly Lys Ile Ala Asp Tyr Asn Tyr Lys Leu Pro Asp Asp Phe Thr
115 120 125

Gly Cys Val Ile Ala Trp Asn Ser Asn Asn Leu Asp Ser Lys Val Gly
130 135 140

Gly Asn Tyr Asn Tyr Leu Tyr Arg Leu Phe Arg Lys Ser Asn Leu Lys
145 150 155 160

Pro Phe Glu Arg Asp Ile Ser Thr Glu Ile Tyr Gln Ala Gly Ser Thr
165 170 175

Pro Cys Asn Gly Val Glu Gly Phe Asn Cys Tyr Phe Pro Leu Gln Ser
180 185 190

Tyr Gly Phe Gln Pro Thr Asn Gly Val Gly Tyr Gln Pro Tyr Arg Val
195 200 205

Val Val Leu Ser Phe Glu Leu Leu His Ala Pro Ala Thr Val Cys Gly
210 215 220

Pro Lys Lys Ser Thr Asn Leu Val Lys Asn Lys Cys Val Asn Phe Thr
225 230 235 240

Ser Arg Arg Arg Arg Arg Arg Lys Lys Gly Arg His His His His His
245 250 255

His

<210> SEQ ID NO 37
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MH

<400> SEQUENCE: 37

Met Phe Val Phe Leu Val Leu Leu Pro Leu Val Ser Ser Gln Cys Val
1 5 10 15

Arg Val Gln Pro Thr Glu Ser Ile Val Arg Phe Pro Asn Ile Thr Asn
20 25 30

```
Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys His Arg His His His His His
                245                 250                 255

His


<210> SEQ ID NO 38
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MI

<400> SEQUENCE: 38

Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125
```

```
Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Ile Arg His His His His His
                245                 250                 255

His


<210> SEQ ID NO 39
<211> LENGTH: 257
<212> TYPE: PRT
<213> ORGANISM: Artificial Sequence
<220> FEATURE:
<223> OTHER INFORMATION: SARS-CoV-2 RBD-LRRC24P-ML

<400> SEQUENCE: 39

Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
```

225 230 235 240

Ser Arg Arg Arg Arg Arg Arg Lys Lys Leu Arg His His His His His
245 250 255

His

<210> SEQ ID NO 40
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MK

<400> SEQUENCE: 40

Met Phe Val Phe Leu Val Leu Leu Pro Leu Val Ser Ser Gln Cys Val
1 5 10 15

Arg Val Gln Pro Thr Glu Ser Ile Val Arg Phe Pro Asn Ile Thr Asn
20 25 30

Leu Cys Pro Phe Gly Glu Val Phe Asn Ala Thr Arg Phe Ala Ser Val
35 40 45

Tyr Ala Trp Asn Arg Lys Arg Ile Ser Asn Cys Val Ala Asp Tyr Ser
50 55 60

Val Leu Tyr Asn Ser Ala Ser Phe Ser Thr Phe Lys Cys Tyr Gly Val
65 70 75 80

Ser Pro Thr Lys Leu Asn Asp Leu Cys Phe Thr Asn Val Tyr Ala Asp
85 90 95

Ser Phe Val Ile Arg Gly Asp Glu Val Arg Gln Ile Ala Pro Gly Gln
100 105 110

Thr Gly Lys Ile Ala Asp Tyr Asn Tyr Lys Leu Pro Asp Asp Phe Thr
115 120 125

Gly Cys Val Ile Ala Trp Asn Ser Asn Asn Leu Asp Ser Lys Val Gly
130 135 140

Gly Asn Tyr Asn Tyr Leu Tyr Arg Leu Phe Arg Lys Ser Asn Leu Lys
145 150 155 160

Pro Phe Glu Arg Asp Ile Ser Thr Glu Ile Tyr Gln Ala Gly Ser Thr
165 170 175

Pro Cys Asn Gly Val Glu Gly Phe Asn Cys Tyr Phe Pro Leu Gln Ser
180 185 190

Tyr Gly Phe Gln Pro Thr Asn Gly Val Gly Tyr Gln Pro Tyr Arg Val
195 200 205

Val Val Leu Ser Phe Glu Leu Leu His Ala Pro Ala Thr Val Cys Gly
210 215 220

Pro Lys Lys Ser Thr Asn Leu Val Lys Asn Lys Cys Val Asn Phe Thr
225 230 235 240

Ser Arg Arg Arg Arg Arg Arg Lys Lys Lys Arg His His His His His
245 250 255

His

<210> SEQ ID NO 41
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MM

<400> SEQUENCE: 41

Met Phe Val Phe Leu Val Leu Leu Pro Leu Val Ser Ser Gln Cys Val
1 5 10 15

```
Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Met Arg His His His His His
                245                 250                 255

His
```

<210> SEQ ID NO 42
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MF

<400> SEQUENCE: 42

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110
```

```
Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Phe Arg His His His His His
                245                 250                 255

His


<210> SEQ ID NO 43
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MP

<400> SEQUENCE: 43

Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
```

```
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Pro Arg His His His His His
                245                 250                 255

His


<210> SEQ ID NO 44
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MT

<400> SEQUENCE: 44

Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Thr Arg His His His His His
                245                 250                 255

His


<210> SEQ ID NO 45
<211> LENGTH: 257
<212> TYPE: PRT
<213> ORGANISM: Artificial Sequence
<220> FEATURE:
<223> OTHER INFORMATION: SARS-CoV-2 RBD-LRRC24P-MW

<400> SEQUENCE: 45
```

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Trp Arg His His His His His
                245                 250                 255

His
```

<210> SEQ ID NO 46
<211> LENGTH: 256
<212> TYPE: PRT
<213> ORGANISM: Artificial Sequence
<220> FEATURE:
<223> OTHER INFORMATION: SARS-CoV-2 RBD-LRRC24P-M7

<400> SEQUENCE: 46

```
Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95
```

-continued

```
Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205

Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Lys Lys Ala Arg His His His His His His
                245                 250                 255


<210> SEQ ID NO 47
<211> LENGTH: 256
<212> TYPE: PRT
<213> ORGANISM: Artificial Sequence
<220> FEATURE:
<223> OTHER INFORMATION: SARS-CoV-2 RBD-LRRC24P-M8

<400> SEQUENCE: 47

Met Phe Val Phe Leu Val Leu Leu Pro Leu Val Ser Ser Gln Cys Val
1               5                   10                  15

Arg Val Gln Pro Thr Glu Ser Ile Val Arg Phe Pro Asn Ile Thr Asn
            20                  25                  30

Leu Cys Pro Phe Gly Glu Val Phe Asn Ala Thr Arg Phe Ala Ser Val
        35                  40                  45

Tyr Ala Trp Asn Arg Lys Arg Ile Ser Asn Cys Val Ala Asp Tyr Ser
    50                  55                  60

Val Leu Tyr Asn Ser Ala Ser Phe Ser Thr Phe Lys Cys Tyr Gly Val
65                  70                  75                  80

Ser Pro Thr Lys Leu Asn Asp Leu Cys Phe Thr Asn Val Tyr Ala Asp
                85                  90                  95

Ser Phe Val Ile Arg Gly Asp Glu Val Arg Gln Ile Ala Pro Gly Gln
            100                 105                 110

Thr Gly Lys Ile Ala Asp Tyr Asn Tyr Lys Leu Pro Asp Asp Phe Thr
        115                 120                 125

Gly Cys Val Ile Ala Trp Asn Ser Asn Asn Leu Asp Ser Lys Val Gly
    130                 135                 140

Gly Asn Tyr Asn Tyr Leu Tyr Arg Leu Phe Arg Lys Ser Asn Leu Lys
145                 150                 155                 160

Pro Phe Glu Arg Asp Ile Ser Thr Glu Ile Tyr Gln Ala Gly Ser Thr
                165                 170                 175

Pro Cys Asn Gly Val Glu Gly Phe Asn Cys Tyr Phe Pro Leu Gln Ser
            180                 185                 190

Tyr Gly Phe Gln Pro Thr Asn Gly Val Gly Tyr Gln Pro Tyr Arg Val
        195                 200                 205
```

```
Val Val Leu Ser Phe Glu Leu Leu His Ala Pro Ala Thr Val Cys Gly
    210                 215                 220

Pro Lys Lys Ser Thr Asn Leu Val Lys Asn Lys Cys Val Asn Phe Thr
225                 230                 235                 240

Ser Arg Arg Arg Arg Arg Arg Lys Lys Ala His His His His His His
                245                 250                 255


<210> SEQ ID NO 48
<211> LENGTH: 223
<212> TYPE: PRT
<213> ORGANISM: Artificial Sequence
<220> FEATURE:
<223> OTHER INFORMATION: 2019 nCoV RBD

<400> SEQUENCE: 48

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 49
<211> LENGTH: 222
<212> TYPE: PRT
<213> ORGANISM: Artificial Sequence
<220> FEATURE:
<223> OTHER INFORMATION: SARS RBD

<400> SEQUENCE: 49

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45
```

-continued

```
Val Leu Tyr Asn Ser Thr Phe Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
        115                 120                 125

Gly Asn Tyr Asn Tyr Lys Tyr Arg Tyr Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
                165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
    210                 215                 220


<210> SEQ ID NO 50
<211> LENGTH: 70
<212> TYPE: PRT
<213> ORGANISM: Artificial Sequence
<220> FEATURE:
<223> OTHER INFORMATION: SARS-CoV-2 signal peptide

<400> SEQUENCE: 50

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val
65                  70
```

HIGH-POTENCY SARS CORONAVIRUS 2 ANTIGEN AND VACCINE COMPOSITION COMPRISING SAME

SEQUENCE LISTING

The Sequence Listing submitted in text format (.txt) filed on Dec. 19, 2025, named "SequenceListing.txt", created on Dec. 17, 2025 (60,650 bytes), is incorporated herein by reference.

BACKGROUND

Technical Field

The present invention relates to a vaccine production technology for controlling SARS coronavirus 2 (Severe Acute Respiratory Syndrome Coronavirus 2, SARS-CoV-2), which causes Coronavirus disease 2019 (COVID-19, (novel coronavirus 2019-nCoV). The present technology particularly relates to a recombinant antigen using SARS-CoV-2 receptor-binding domain (RBD) fused with a cell membrane penetrating domain derived from human LRRC24 protein (Leucine rich repeat containing 24, LRRC24) as an antigen, and a vaccine composition comprising the same in order to produce a high-potency vaccine.

Background Art

SARS-COV-2 is an enveloped virus with a genome of about 30,000 base pairs of positive-strand single-stranded RNA. Since it was first reported in Wuhan, China from December 2019, the number of infectious patients worldwide has been increasing explosively (Non-Patent Document 1). As a result of analyzing the viral gene sequence, it is a virus showing about 79% similarity to severe acute respiratory syndrome coronavirus (SARS-COV) and about 50% similarity to Middle East respiratory syndrome coronavirus (MERS-COV) (Non-Patent Document 1). Coronaviruses induce infection in host cells after binding to receptors by expressing spike proteins on the surface of the virus. Receptor binding domain (RBD) that binds to a receptor exists in these spike proteins, and it is reported in Non-Patent Document 2 that the structures of the core subdomains in various coronaviruses are very similar. Based on the similarity of these receptor binding domains, receptor binding domain present in the spike protein of SARS-COV-2 can be identified. In the case of MERS-COV or SARS-COV, a recombinant vaccine study using receptor binding domain is in progress (Non-Patent Document 3). It can act as a vaccine by inhibiting virus attachment to cells by inducing neutralizing antibodies against receptor binding domain. The present inventors compared the protein sequence similarity with the spike protein of SARS-COV-2 based on the reported SARS-COV receptor binding domain (non-patent document 4), and then selected receptor binding domain of SARS-COV-2. In order to express the receptor binding domain protein in eukaryotic cells, the gene was synthesized by optimizing the codon of the gene sequence expressing the protein. In addition, the signal sequence of the spike protein of SARS-COV-2 was confirmed using a program called SignalP in order to release the protein out of the cell. (http://www.cbs.dtu.dk/services/SignalP/). After cloning into a eukaryotic expression vector, it was confirmed that the antigen was well expressed in eukaryotic cells and that the antigen was well discharged out of the cell.

The cell membrane penetrating domain (LRRC24P) derived from human LRRC24 protein has the characteristic of being able to permeate the fused protein into a cell. When this is fused to a recombinant immunogen, it is possible to activate the immune cell by penetrating the immunogen into the immune cell with the ability to generate the existing neutralizing antibody. Through this, it is possible to manufacture a high-efficiency vaccine by improving the vaccine ability of the recombinant antigen.

BRIEF DESCRIPTION OF THE INVENTION

Technical Problem

The present invention has been derived from the above needs, and the present inventors completed the present invention by confirming the effect on the recombinant antigen comprising a cell membrane permeation domain comprising polypeptide derived from a human LRRC24 and SARS-CoV-2 antigen or a fragment thereof; or vaccine composition comprising the same.

Technical Solution

In order to solve the above problems, the present invention provides a recombinant antigen comprising a cell membrane permeation domain comprising a polypeptide of any one of SEQ ID NOs: 1 to 22 derived from human LRRC24 and a SARS-CoV-2 antigen or a fragment thereof;

Also, the present invention provides a gene construct comprising a polynucleotide encoding a recombinant antigen comprising a cell membrane permeation domain comprising a polypeptide of any one of SEQ ID NOs: 1 to 22 derived from human LRRC24 and a SARS-CoV-2 antigen or a fragment thereof;

In another embodiment, the present invention provides a recombinant vector comprising a gene construct comprising a polynucleotide encoding a recombinant antigen comprising a cell membrane permeation domain comprising a polypeptide of any one of SEQ ID NOs: 1 to 22 derived from human LRRC24 and a SARS-CoV-2 antigen or a fragment thereof;

The present invention provides a vaccine composition comprising a recombinant antigen comprising a cell membrane permeation domain comprising a polypeptide of any one of SEQ ID NOs: 1 to 22 derived from human LRRC24 and a SARS-CoV-2 antigen or a fragment thereof;

As another example, the present invention provides a method for producing a SARS-CoV-2 recombinant antigen comprising:

- a step of identifying the gene or amino acid sequence of the SARS-CoV-2 antigen or fragment thereof;
- a step of binding of a cell membrane permeation domain comprising a polypeptide of any one of SEQ ID NOs: 1 to 22 derived from human LRRC24
- a step of preparing a recombinant antigen in which an antigen and a cell membrane penetrating domain are fused in a system for overexpressing an immunogen in human cells;
- a step of purifying the recombinant antigen Also, the present invention provides a kit for preventing or treating SARS-CoV-2 infection comprising a vaccine composition and instructions for use comprising a recombinant antigen comprising a cell membrane permeation domain comprising a polypeptide of any one of SEQ ID NOs: 1 to 22 derived from human LRRC24 and a SARS-CoV-2 antigen or a fragment thereof;

Effects of the Invention

The recombinant antigen of SARS-CoV-2 receptor binding domain (RBD) fused with cell membrane penetrating domain (LRRC24P) derived from the human LRRC24 protein according to the present invention can effectively prevent SARS-CoV-2 infection, and can be usefully used to produce a novel high-potency recombinant vaccine.

BRIEF DESCRIPTION OF THE DRAWINGS

FIG. 1 shows a comparison result of the amino acid sequence of SARS-COV-2 receptor binding domain (SEQ ID NO: 48) and SARS coronavirus receptor binding domain of Example 1 (SEQ ID NO: 49) according to an embodiment of the present invention (FIG. 1*a*) and SARS-CoV-2 signal peptide sequence (SEQ ID NO: 50) analysis result (FIG. 1*b*). And, the schematic diagram (FIG. 1*c*) of the recombinant SARS-COV-2 antigen structure fused with the cell membrane penetrating domain (LRRC24P) derived from the human LRRC24 protein is shown.

FIG. 2 shows the results of verifying the purified antigen through coomassie blue staining (A) and Western blot analysis using an antibody specific for SARS-CoV-2 spike protein (B), after the two types of SARS-CoV-2 antigens of Example 1 according to an embodiment of the present invention were purified in large quantities using animal cells, FIG. 3 shows a schematic diagram (A) showing the process of obtaining serum for evaluation of neutralizing antibody production ability by inoculating C57/BL6 mice with the recombinant SARS-CoV-2 antigen of Example 2 according to an embodiment of the present invention, and the result (B, C) of confirming the neutralizing antibody titer of SARS-CoV-2 generated in the serum through Focus reduction neutralization test (FRNT)

FIG. 4 shows a schematic diagram (A) showing the process of inoculating C57/BL6 mice with the recombinant SARS-CoV-2 antigen of Example 2 according to an embodiment of the present invention, and obtaining serum for evaluation of antigen-specific immunoglobulin G production ability, and the result (B) of confirming the production of SARS-CoV-2 RBD-specific immunoglobulin G in serum through ELISA assay.

DETAILED DESCRIPTION OF THE INVENTION

Hereinafter, preferred embodiments of the present invention will be described in detail. In addition, in the following description, many specific details such as specific components are shown, which are provided to help a more general understanding of the present invention, and it will be apparent to those skilled in the art that the present invention may be practiced without these specific details. And, in describing the present invention, if it is determined that a detailed description of a related known function or configuration may unnecessarily obscure the gist of the present invention, the detailed description thereof will be omitted.

The present invention provides a recombinant antigen comprising a cell membrane permeation domain comprising a polypeptide of any one of SEQ ID NOs: 1 to 22 derived from human LRRC24 and a SARS-CoV-2 antigen or a fragment thereof;

The present invention is obtained in the same way as domestic application No. 10-2019-0144779, a cell membrane permeation domain comprising a polypeptide of any one of SEQ ID NOs: 1 to 22 derived from human LRRC24 protein according to an embodiment of the present invention.

The SARS-CoV-2 antigen according to an embodiment of the present invention refers to all antigenic components included in SARS-CoV-2, preferably the recombinant antigen comprising any one or more selected from the group consisting of inactivated whole SARS-CoV-2 antigen, spike protein, nucleoprotein, envelope, S1 domain, S2 domain, receptor binding domain (RBD), N terminus, C terminus and fragments thereof, and more preferably, a receptor binding domain (RBD), and still more preferably, SEQ ID NO: 24 or a fragment thereof, but is not limited thereto.

The recombinant antigen according to one embodiment of the present invention comprises the number of all cases combined a cell membrane permeation domain comprising a polypeptide of any one of SEQ ID NOs: 1 to 22 derived from human LRRC24 and a SARS-CoV-2 antigen or a fragment thereof, and preferably a recombinant antigen comprising at least one selected from the group consisting of SEQ ID NOs: 26 to 47, but is not limited thereto.

Also the present invention provides gene construct comprising a polynucleotide encoding a recombinant antigen comprising a cell membrane permeation domain comprising a polypeptide of any one of SEQ ID NOs: 1 to 22 derived from human LRRC24 and a SARS-CoV-2 antigen or a fragment thereof;

In the gene construct of the present invention, the nucleotide sequence is preferably present in a suitable expression construct. In the expression construct, the nucleotide sequence is preferably operably linked to a promoter.

As used herein, the term "operably linked" refers to a functional linkage between a nucleic acid expression control sequence (e.g., an array of promoters, signal sequences, or transcriptional regulator binding sites) and another nucleic acid sequence, whereby the control sequence regulates the transcription and/or translation of the other nucleic acid sequence.

As another example, the present invention provides a recombinant vector comprising a gene construct comprising a polynucleotide encoding a recombinant antigen comprising a cell membrane permeation domain comprising a polypeptide of any one of SEQ ID NOs: 1 to 22 derived from human LRRC24 and a SARS-CoV-2 antigen or a fragment thereof;

The present invention provides a vaccine composition comprising recombinant antigen comprising a cell membrane permeation domain comprising a polypeptide of any one of SEQ ID NOs: 1 to 22 derived from human LRRC24 and a SARS-CoV-2 antigen or a fragment thereof;

In one embodiment of the present invention, the vaccine composition has a specific neutralizing ability of SARS-CoV-2 and is for preventing or treating SARS-CoV-2 infection, but is not limited thereto.

The vaccine composition of the present invention includes a pharmaceutically acceptable carrier in addition to the active ingredient. A pharmaceutically acceptable carrier included in the vaccine composition of the present invention is commonly used in formulation, and comprises lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydride hydroxybenzoate, propylhydroxybenzoate, talc, magnesium stearate and mineral oil, and the like, but is not limited thereto. The vaccine composition of the present invention may further include a lubricant, a wetting agent, a sweetening agent, a flavoring agent, an emulsifying agent, a suspending agent, a preservative, etc. in addition to the above components. Suitable pharmaceutically acceptable carriers and agents are described in detail in Remington's Pharmaceutical Sciences (19th ed., 1995).

In addition, the vaccine composition of the present invention is formulated in a unit dosage form by using a pharmaceutically acceptable carrier and/or excipient according to a method that can be easily carried out by a person of ordinary skill in the art to which the present invention pertains or can be prepared by incorporation into a multidose container. Vaccine compositions may be formulated using methods known in the art to permit rapid, or sustained or delayed release of the active ingredient upon administration to a mammal. Formulations include powders, granules, tablets, emulsions, syrups, aerosols, soft or hard gelatin capsules, sterile injectable solutions, and sterile powder forms, but is not limited thereto.

A suitable dosage of the vaccine composition of the present invention may be prescribed variously depending on factors such as formulation method, administration mode, age, weight, sex, pathological condition, food, administration time, administration route, excretion rate, and response sensitivity of the patient. Otherwise, the dosage of the pharmaceutical composition of the present invention is preferably 0.001-1000 mg/kg (body weight) per day, but is not limited thereto.

The vaccine composition can be injected into humans or non-human animals to increase the antibody production rate against the antigen, and the injection may be performed by any one method selected from the group consisting of subcutaneous injection, intramuscular injection, intraperitoneal injection, nasal administration, oral administration, transdermal administration and oral administration.

The vaccine composition according to an embodiment of the present invention may additionally include an adjuvant composition, an immunostimulator or an adjuvant to increase efficacy. Vaccine adjuvants are largely classified into three types according to their mechanism of action: antigen carriers, immune enhancers, and those that stimulate immune responses and act as a matrix for antigens. Effective use of vaccine adjuvants can have various effects, such as (1) increasing the immunogenicity of recombinant antigens, (2) reducing antigen doses or reduce the number of immunizations, and (3) improving immunogenicity in infants and the elderly with weakened immunity. As the vaccine adjuvant, an adjuvant component known in the art may be used, preferably aluminum salt, MF59, AS03, AS04, etc. may be used alone or in combination, and more preferably, alum may be used, but is not limited thereto.

As another example, the present invention provides a method for producing a SARS-CoV-2 recombinant antigen comprising:

the step of identifying the gene or amino acid sequence of the SARS-CoV-2 antigen or fragment thereof;

the step of binding of a cell membrane permeation domain comprising a polypeptide of any one of SEQ ID NOs: 1 to 22 derived from human LRRC24 the step of preparing a recombinant antigen in which an antigen and a cell membrane penetrating domain are fused in a system for overexpressing an immunogen in human cells;

the step of purifying the recombinant antigen;

The present invention also provides a kit for preventing or treating SARS-CoV-2 infection comprising a vaccine composition and instructions for use comprising a recombinant antigen comprising a cell membrane permeation domain comprising a polypeptide of any one of SEQ ID NOs: 1 to 22 derived from human LRRC24 and a SARS-CoV-2 antigen or a fragment thereof;

Advantages and features of the present invention, and methods of achieving them, will become apparent with reference to the embodiments described below in detail. However, the present invention is not limited to the embodiments disclosed below, but will be implemented in various different forms, and only the present embodiments are provided so that the disclosure of the present invention is complete, and to completely inform those of ordinary skill in the art to which the present invention belongs, the scope of the invention, and the invention is only defined by the scope of the claims.

<Example 1> Production and Purification of Recombinant Antigen of SARS-CoV-2 Receptor Binding Domain (RBD) Fused with a Cell Membrane Permeation Domain Derived from Human LRRC24 (Leucine Rich Repeat Containing 24) Protein A nucleotide sequence expressing the Spike protein was obtained using the published SARS-CoV-2 gene sequence (GenBank ID: MN908974.3). The corresponding amino acid sequence was compared with the previously known SARS-CoV-2 receptor binding domain for homology using the amino acid sequence align tool on the SnapGene program (FIG. 1*a*). Through this, the amino acid sequence of the novel coronavirus receptor binding domain was obtained. Receptor binding domain corresponds to amino acids 319 to 541 of the novel coronavirus spike protein. In order to express the corresponding gene sequence in eukaryotic cells, after codon optimization was performed, the gene synthesis was performed by IDT company. In addition, since releasing the protein out of the cell helps in protein expression and purification, a signal peptide responsible for the release of the novel coronavirus spike protein was revealed (FIG. 1*b*). Through an analysis program called SignalP, it was confirmed that 1 to 16 amino acids of the spike protein could play this role, and this was used for immunogen expression.

A recombinant antigen of the SARS-CoV-2 receptor binding domain (RBD) fused to cell membrane penetrating domain (LRRC24P) derived from the human LRRC24 protein was constructed using a system that overexpresses an immunogen in human cells (FIG. 1*c*). For efficient protein purification, an immunogen (SARS-CoV-2 RBD) in which six histidine amino acid tags were fused to the C-terminus of SARS-CoV-2 RBD was prepared. To study the vaccine efficacy improvement function of cell membrane penetrating domain (LRRC24P) derived from the human LRRC24 protein, a fused SARS-CoV-2 RBD-LRRC24P antigen was prepared. Both antigens had a His-tag, so they were purified using a Ni-NTA agarose column (QIAGEN). The bulk purified recombinant antigen was confirmed by Coomassie blue staining (FIG. 2A) and Western blot analysis (FIG. 2B). A high-purity immunogen was produced and used to evaluate vaccine efficacy.

<Example 2> Immunization and Determination of Neutralizing Antibody Titers in Wild-Type Mice of Recombinant Antigen of SARS-CoV-2 Receptor Binding Domain (RBD) Fused with a Cell Membrane Permeation Domain Derived from Human LRRC24 Protein Recombinant antigens of SARS-CoV-2 receptor binding domain (RBD) fused with a cell membrane permeation domain derived from human LRRC24 obtained in Example 1 were immunized according to the study schedule presented in FIG. 3A. Recombinant immunogen was inoculated using 10 micrograms per mouse. Each antigen was tested using 6 mice per group. As an adjuvant, Alum from Thermo Fisher Scientific was used. The first immunization (priming) was performed on day 0 by injecting the mouse intramuscularly with the immunogen. The immunization was repeated on the 14th (2nd) and 28th (3rd) days for immune boosting. After three vaccinations, mouse serum was obtained according to the schedule shown in FIG. 3A and neutralizing antibody titers were measured. To measure the neutralizing antibody titer against SARS-CoV-2, mouse serum was diluted 40-fold in minimal essential medium, and reacted with SARS-CoV-2 at 37° C. The viral serum mixture was added to the monolayer cells cultured in 96-well flasks and then incubated in a 5% carbon dioxide incubator at 37° C. for 8 hours. In the control group without neutralizing antibody, the specific antibody reaction effect by SARS-CoV-2 occurs well. In the presence of a neutralizing antibody, the effect of the antibody reaction specific to SARS-CoV-2 does not occur well. This was quantitatively measured through a focus reduction neutralization test (FRNT) assay, and the level of neutralizing antibody was quantified by calculating a dilution factor representing 50% of the intracellular SARS-CoV-2 specific antibody level.

As the result shown in FIG. 4, it was confirmed that the neutralizing antibody produced in mice immunized with the recombinant antigen of the SARS-CoV-2 receptor binding domain (RBD) fused to cell membrane penetrating domain (LRRC24P) derived from the human LRRC24 protein produced immunoglobulin G specific for the SARS-CoV-2 Receptor binding domain (RBD). (FIGS. 4A and 4B)

What is claimed is:

1. A recombinant antigen comprising a cell membrane permeation domain consisting of a polypeptide selected from the group consisting of SEQ ID NOS: 1 to 22 derived from human leucine-rich repeat-containing protein 24 (LRRC24) and a severe acute respiratory syndrome coronavirus type 2 (SARS-COV-2) receptor binding domain (RBD).

2. The recombinant antigen according to claim 1, wherein the SARS-COV-2 RBD comprises SEQ ID NO: 24.

3. The recombinant antigen according to claim 1, wherein the recombinant antigen comprises at least one sequence selected from the group consisting of SEQ ID NOS: 26 to 47.

4. A gene construct comprising a polynucleotide encoding the recombinant antigen according to claim 1.

5. A recombinant vector comprising the gene construct according to claim 4.

6. A vaccine composition comprising the recombinant antigen according to claim 1.

7. The vaccine composition according to claim 6, wherein the vaccine composition has a SARS-COV-2 specific neutralizing ability.

8. The vaccine composition according to claim 6, wherein the vaccine composition is for preventing or treating SARS-COV-2 infection.

9. A method for producing a SARS-COV-2 recombinant antigen comprising:

a step of identifying the gene or amino acid sequence of an immunogenic SARS-COV-2 RBD;

a step of identifying a cell membrane permeation domain consisting of a polypeptide selected from the group consisting of SEQ ID NOS: 1 to 22 derived from human LRRC24;

a step of preparing the SARS-COV-2 recombinant antigen by engineering both the immunogenic SARS COV-2 RBD and the cell membrane permeation domain together as a fusion protein in an expression system, wherein said expression system is designed to overexpress said fusion protein in human cells; and a step of purifying the SARS-COV-2 recombinant antigen.

10. A kit for preventing or treating SARS-COV-2 infection comprising a vaccine composition and instructions for use, the vaccine composition comprising a recombinant antigen comprising a cell membrane permeation domain consisting of a polypeptide selected from the group consisting of SEQ ID NOS: 1 to 22 derived from human LRRC24, and a SARS-COV-2 RBD.

* * * * *